(12) United States Patent
Meng et al.

(10) Patent No.: US 12,403,298 B2
(45) Date of Patent: Sep. 2, 2025

(54) PHYSIOTHERAPY DEVICE AND METHOD FOR CONTROLLING PHYSIOTHERAPY DEVICE

(71) Applicant: Hi-Dow IPHC, Inc., St. Louis, MO (US)

(72) Inventors: Luying Meng, Hefei (CN); Yang Chen, Hefei (CN); Bin Du, Hefei (CN); Qiangsheng Sun, Hefei (CN)

(73) Assignee: Hi-Dow IPHC, Inc., St. Louis, MO (US)

( * ) Notice: Subject to any disclaimer, the term of this patent is extended or adjusted under 35 U.S.C. 154(b) by 407 days.

(21) Appl. No.: 17/870,808

(22) Filed: Jul. 21, 2022

(65) Prior Publication Data
US 2023/0062845 A1 Mar. 2, 2023

(51) Int. Cl.
*A61N 1/04* (2006.01)
*A61N 1/40* (2006.01)

(52) U.S. Cl.
CPC ........... *A61N 1/0456* (2013.01); *A61N 1/403* (2013.01)

(58) Field of Classification Search
None
See application file for complete search history.

(56) References Cited

U.S. PATENT DOCUMENTS

| | | | | |
|---|---|---|---|---|
| 2005/0113738 | A1* | 5/2005 | Fuchita | A61N 1/0436 604/20 |
| 2008/0312580 | A1* | 12/2008 | Barsness | A61N 1/044 604/20 |
| 2017/0216592 | A1* | 8/2017 | Dai | A61F 7/02 |
| 2020/0139106 | A1* | 5/2020 | Chen | H05B 6/105 |
| 2020/0188154 | A1* | 6/2020 | Hsu | A61H 7/004 |
| 2023/0372724 | A1* | 11/2023 | Casalino | A61N 2/02 |

FOREIGN PATENT DOCUMENTS

CN 113082520 A * 7/2021

* cited by examiner

*Primary Examiner* — Benjamin J Klein
*Assistant Examiner* — Willow Grace Welch
(74) *Attorney, Agent, or Firm* — Arch & Lake LLP (57) ABSTRACT

A physiotherapy device and a method for controlling the physiotherapy device are provided. The physiotherapy device may include an electric stimulator capable of generating electric pulses, a heating electrode sheet capable of attaching to a user's body, and a connecting component configured to connect with the heating electrode sheet via a plurality of fastening components and configured to connect with the electric stimulator via an electric pulse transmission cable. Furthermore, each fastening component may include a first fastener and a second fastener that are connected with each other. The plurality of fastening components may include a heating fastening component, a heat measuring fastening component, and at least one electric pulse fastening component, the heating fastening component transmits current to the heating electrode sheet so as to provide heat, and the heat measuring fastening component measures a temperature of the heating electrode sheet.

20 Claims, 5 Drawing Sheets

PHYSIOTHERAPY DEVICE AND METHOD FOR CONTROLLING PHYSIOTHERAPY DEVICE

CROSS-REFERENCE TO RELATED APPLICATION

This application is based upon and claims priority to Chinese Patent Application No. 202121998013.4 filed on Aug. 24, 2021, the entire contents thereof are incorporated herein by reference for all purposes.

TECHNICAL FIELD

This disclosure is related to a physiotherapy device. More specifically, this disclosure relates to a physiotherapy device with multiple purposes.

BACKGROUND

Most of physiotherapy devices including electronic muscle stimulators have complicated structures but a single function. These physiotherapy devices can realize only a single electric pulse function or a single heating function, which cannot meet the need of multiple functions, such as both electric pulse and heating functions, in a single device.

SUMMARY

The present disclosure provide a physiotherapy device and a method for controlling the physiotherapy device thereof.

According to a first aspect of the present disclosure, a physiotherapy device is provided. The physiotherapy device may include an electric stimulator capable of generating electric pulses. The physiotherapy device may include a heating electrode sheet capable of attaching to a user's body. The physiotherapy device may include a connecting component configured to connect with the heating electrode sheet via a plurality of fastening components and configured to connect with the electric stimulator via an electric pulse transmission cable. Furthermore, each fastening component may include a first fastener and a second fastener that are connected with each other, the first fastener is disposed on a midline of the connecting component and the second fastener disposed on a midline of the heating electrode sheet.

Moreover, the plurality of fastening components may include a heating fastening component, a heat measuring fastening component, and at least one electric pulse fastening component, the heating fastening component transmits current to the heating electrode sheet so as to provide heat, and the heat measuring fastening component measures a temperature of the heating electrode sheet. Further, the connecting component may be configured to receive the electric pulses generated by the electric stimulator via the electric pulse transmission cable, to adjust the received electric pulses, and to transmit the adjusted electric pulses via the at least one electric pulse fastening component.

According to a second aspect of the present disclosure, a method for controlling a physiotherapy device is provided. The method may include providing an electric stimulator capable of generating electric pulses. The method may include providing a heating electrode sheet capable of attaching to a user's body. The method may include providing a connecting component configured to connect with the heating electrode sheet via a plurality of fastening components and configured to connect with the electric stimulator via an electric pulse transmission cable. Furthermore, the method may include providing each fastening component including a first fastener and a second fastener that are connected with each other, disposing the first fastener on a midline of the connecting component and disposing the second fastener on a midline of the heating electrode sheet.

Moreover, the method may include providing the plurality of fastening components including a heating fastening component, a heat measuring fastening component, and at least one electric pulse fastening component, where the heating fastening component transmits current to the heating electrode sheet so as to provide heat, and the heat measuring fastening component measures a temperature of the heating electrode sheet. The method may include configuring the connecting component to receive the electric pulses generated by the electric stimulator via the electric pulse transmission cable, to adjust the received electric pulses, and to transmit the adjusted electric pulses via the at least one electric pulse fastening component.

It is to be understood that the above general descriptions and detailed descriptions below are only exemplary and explanatory and not intended to limit the present disclosure.

BRIEF DESCRIPTION OF THE DRAWINGS

The accompanying drawings, which are incorporated in and constitute a part of this specification, illustrate examples consistent with the present disclosure and, together with the description, serve to explain the principles of the disclosure.

DETAILED DESCRIPTION

Reference will now be made in detail to example embodiments, examples of which are illustrated in the accompanying drawings. The following description refers to the accompanying drawings in which the same numbers in different drawings represent the same or similar elements unless otherwise represented. The implementations set forth in the following description of example embodiments do not represent all implementations consistent with the disclosure. Instead, they are merely examples of apparatuses and methods consistent with aspects related to the disclosure as recited in the appended claims.

The terminology used in the present disclosure is for the purpose of describing particular embodiments only and is not intended to limit the present disclosure. As used in the present disclosure and the appended claims, the singular forms "a," "an," and "the" are intended to include the plural forms as well, unless the context clearly indicates otherwise. It shall also be understood that the term "and/or" used herein is intended to signify and include any or all possible combinations of one or more of the associated listed items.

It shall be understood that, although the terms "first," "second," "third," etc., may be used herein to describe various information, the information should not be limited by these terms. These terms are only used to distinguish one category of information from another. For example, without departing from the scope of the present disclosure, first information may be termed as second information; and similarly, second information may also be termed as first information. As used herein, the term "if" may be understood to mean "when" or "upon" or "in response to a judgment" depending on the context.

Reference throughout this specification to "one embodiment," "an embodiment," "an example," "some embodiments," "some examples," or similar language means that a particular feature, structure, or characteristic described is included in at least one embodiment or example. Features, structures, elements, or characteristics described in connection with one or some embodiments are also applicable to other embodiments, unless expressly specified otherwise.

The terms "module," "sub-module," "circuit," "sub-circuit," "circuitry," "sub-circuitry," "unit," or "sub-unit" may include memory (shared, dedicated, or group) that stores code or instructions that can be executed by one or more processors. A module may include one or more circuits with or without stored code or instructions. The module or circuit may include one or more components that are directly or indirectly connected. These components may or may not be physically attached to, or located adjacent to, one another.

Figure 1:
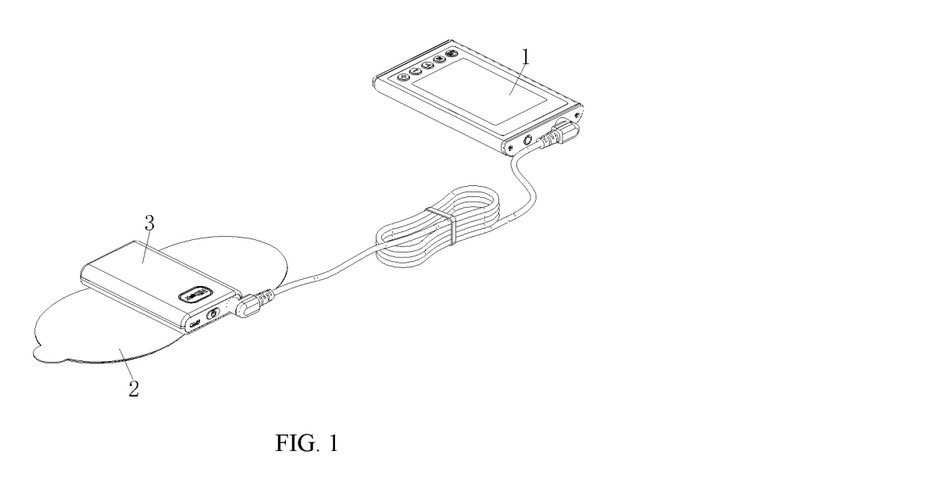
FIG. 1 is a structure diagram of a physiotherapy device with dual functions according to an example of the present disclosure.
Figure 2:
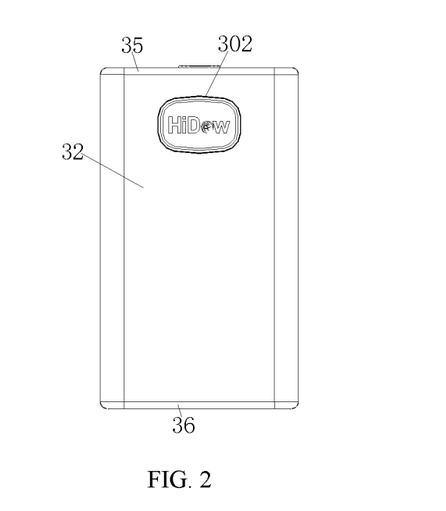
FIG. 2 is a main view of a connecting component according to an example of the present disclosure.
Figure 3:
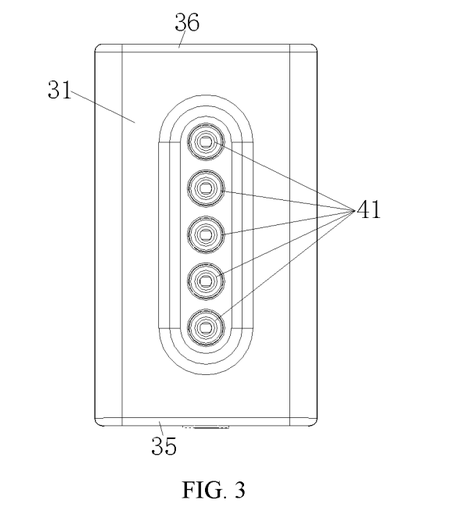
FIG. 3 is a rear view of a connecting component according to an example of the present disclosure.
Figure 4:
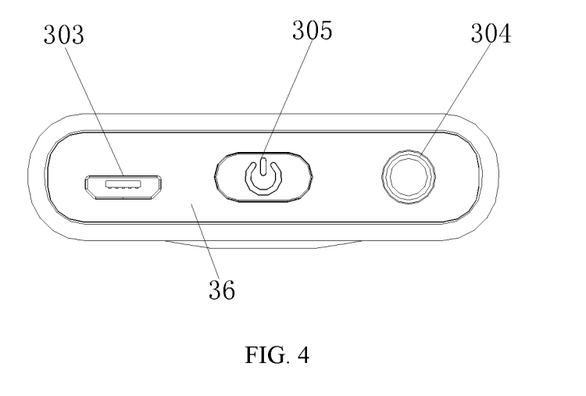
FIG. 4 is an end view of a connecting component according to an example of the present disclosure.
Figure 6:
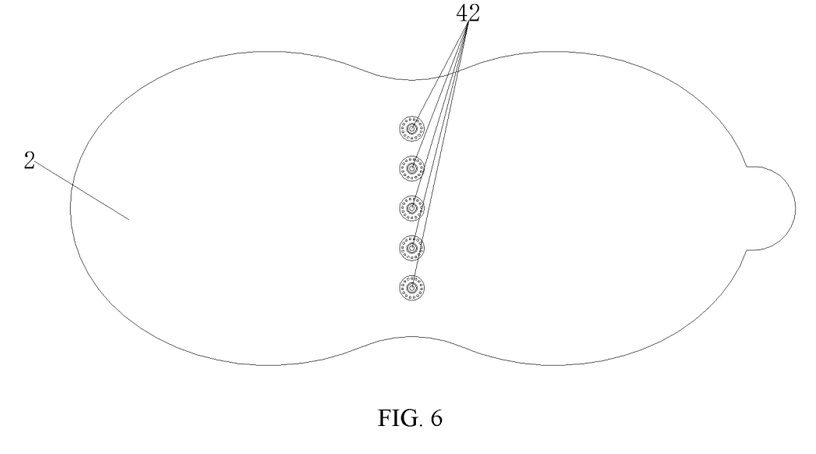
FIG. 6 is a main view of a heating electrode sheet according to an example of the present disclosure.

FIG. 1 is a structure diagram of a physiotherapy device with dual functions according to an example of the present disclosure. As shown in FIG. 1, the physiotherapy device with dual functions include an electric stimulator 1, a heating electrode sheet 2, and a connecting component 3. The connecting component 3 is electrically connected with the electric stimulator 1 and the heating electrode sheet 2. The connecting component 3 is connected to the heating electrode sheet 2 via a plurality of fastening components 4. Furthermore, the connecting component 3 is connected to the electric stimulator 1 via an electric pulse transmission cable. The plurality of fastening components 4 may include a plurality of female fasteners 41 that are disposed in the middle of the connecting component 3. For examples, the plurality of female fasteners 41 are sequentially disposed on a midline of the connecting component 3, as shown in FIG. 3. The plurality of fastening components 4 may further include a plurality of male fasteners 42 that are disposed in the middle of the heating electrode sheet 2. For example, the plurality of male fasteners 42 are located on a midline of the heating electrode sheet 2, as shown in FIG. 6. The plurality of female fasteners 41 are respectively corresponding to the plurality of male fasteners 42.

Further, the connecting component 3 are connected with the heating electrode sheet 2 using the plurality of female fasteners 41 that are respectively corresponding to the plurality of male fasteners 42. The electric pulse transmission cable is electrically connected to the electric stimulator 1 and the heating electrode sheet 2, thus the electric stimulator 1 and the heating electrode sheet 2 are electrically connected via the electric pulse transmission cable. After respectively connecting the connecting component 3 to the heating electrode sheet 2 and the electric stimulator 1, a release film is torn off from the heating electrode sheet 2 and the heating electrode sheet 2 is attached on a user's skin, such as being attached to a part of the skin that needs being affected. Then, the connecting component 3 may be turned on to heat the part of the skin. At the same time, the connecting component 3 is connected to the electric stimulator 1 via the electric pulse transmission cable. The electric stimulator 1 may transmit electric pulses to the heating electrode sheet 2 via the electric pulse transmission cable, and may adjust intensities, modes, and lasting time of the electric pulses, thus implementing electric pulse treatment on the part of the skin, such as exciting neuromuscular tissue of the part of the skin, promoting local blood circulation and analgesia, and relieving anti-inflammatory, swelling, dampness and cold, pain relief, fatigue, etc. The connecting component 3 is connected to the heating electrode sheets via the plurality of fastening components 4, which can implement functions including transmit electric pulses, measuring temperature, heating and fixing, thus ensuring the stability of the physiotherapy device of dual functions.

In some examples according to the present disclosure, in order to ensure the stability of connection between the connecting component 3 and the heating electrode sheet 2, the plurality of female fasteners 41 disposed on the connecting component 3 may include at least two female fasteners 41, and the plurality of male fasteners 42 disposed on the heating electrode sheet 2 may include at least two male fasteners 42. In an example, five female fasteners 41 are located on the connecting component 3 and five male fasteners 42 are located on the heating electrode sheet 2. The five female fasteners 41 or the five male fasteners 42 may respectively include a heating fastener, a heat measuring fastener, a heating and heat measuring fastener, and two electric pulse fasteners. For example, the five female fasteners 41 may include a heating female fastener, a heat measuring female fastener, a heating and heat measuring female fastener, and two electric pulse female fasteners. Additionally, the five male fasteners 42 may include a heating male fastener, a heat measuring male fastener, a heating and heat measuring male fastener, and two electric pulse male fasteners. The heating female fastener is corresponding to the heating male fastener, the heat measuring female fastener is corresponding to the heat measuring male fastener, the heating and heat measuring female fastener is corresponding to the heating and heat measuring male fastener, and the two electric pulse female fasteners are corresponding to the two electric pulse male fasteners. In these examples, the heating electrode sheet 2 can simultaneously implement both heating and temperature measuring using the at least two female fasteners and/or the at least two male fasteners. Furthermore, the heating electrode sheet 2 can be used in parts of a human body with higher curvature than a part without curvature. For example, the heating electrode sheet 2 can be used in bending parts of arms. The bending parts of arms have high curvature. Therefore, the scope of applying the physiotherapy device with dual functions is enlarged.

Figure 5:
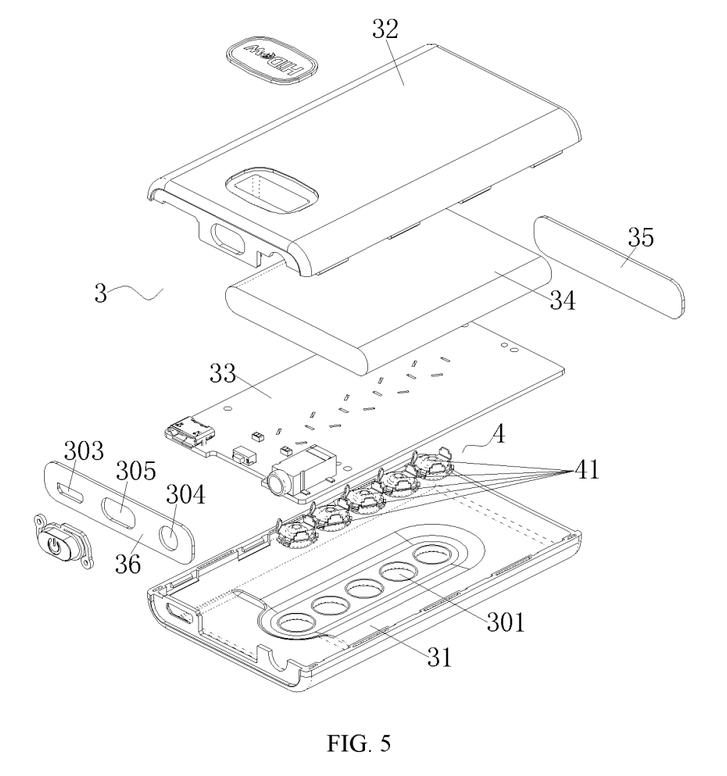
FIG. 5 is an exploded diagram of a connecting component according to an example of the present disclosure.

According to FIGS. 2-5, the connecting component 3 includes a lower connecting housing 31 and an upper connecting housing 32. The connecting component 3 further includes a printed circuit board (PCB) 33 and a built-in lithium battery 34, both of which are built in between the lower connecting housing 31 and the upper connecting housing 32. The connecting component 3 further includes a side cover 35 and a side cover 36 that are respectively located on one side of the lower connecting housing 31 or the upper connecting housing 32, as shown in FIG. 5. A plurality of first fastener holes 301 are disposed on a line in the middle of the lower connecting housing 31. Each of the plurality of first fasteners holes 301 may accommodate one female fastener 41. As shown in FIG. 5, the plurality of first fastener holes 301 are arranged sequentially on the midline of the lower connecting housing 31. Furthermore, at least one light hole 302 is located on a line in the middle of the upper surface of the upper connecting housing 32. As shown in FIG. 5, a light hole 302 is set on the midline of the upper connecting housing 32.

Figure 9:
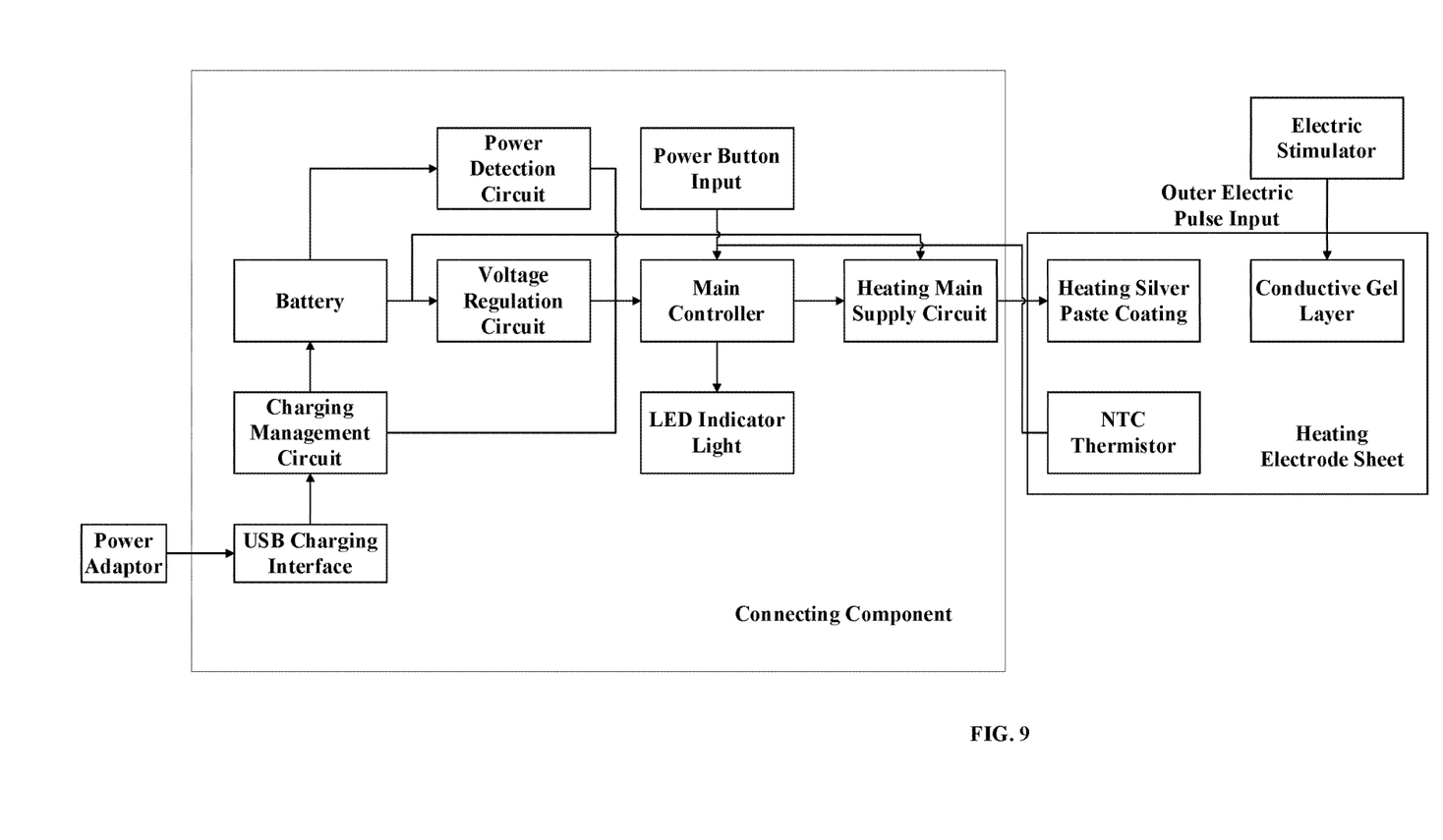
FIG. 9 is a circuit block diagram of a physiotherapy device with dual functions according to an example of the present disclosure.

Moreover, a charging hole 303, a power hole 305, and an input hole 304 are sequentially placed on the top cover 36. The charging hole 303 is capable of accommodating a charging interface on the PCB 33. The input hole 304 is capable of accommodating with an electrical pulse input interface on the PCB 33. The power hole 305 is capable of accommodating a power button. As shown in FIG. 9, a main controller is installed on the PCB 33. Furthermore, a charging management circuit, a voltage regulation circuit, a power detection circuit and a heating main supply circuit are installed on the PCB 33.

When using the physiotherapy device with dual functions, an input by the power button starts the main controller to implement on and off, high temperature control and low temperature control of the physiotherapy device with dual functions. An indicator light installed in the light hole 302 may be a three-color LED indicator light that is directly driven by the main controller. For example, the indicator light is green in the normal working state, the indicator light is red when the power of the built-in lithium battery 34 is low, and the indicator light is blue in the low temperature working mode. Furthermore, the three-color LED indicator light indicates both green and red when the physiotherapy device is in charging. When the physiotherapy device is fully charged, the red light is off and the three-color LED indicator light is green. Moreover, the three-color LED indicator light indicates both blue and red when the physiotherapy device is in the high temperature working mode.

In some examples, the physiotherapy device with dual functions may be powered using the built-in lithium battery 34. The built-in lithium battery 34 may be connected to the power detection circuit. An analog voltage signal is obtained after dividing voltage by a voltage dividing resistor. A negative temperature coefficient (NTC) thermistor 27 in the heating electrode sheet 2 is connected to a circuit in a heating device to obtain an analog voltage signal that is changed. Input and output (I/O) pins are connected to an analog-to-digital (A/D) conversion of the main controller. The main controller converses the analog voltage signal to a numeric variable. Then the actual lithium battery voltage value and the actual operating temperature value are obtained via a program operation. Under normal working conditions, the voltage may be divided into three stages. The first stage is that the voltage U>3.3 V, which means that the built-in lithium battery 34 is determined as low power at this stage and the indicator light is green. The second stage is that the voltage U is between 3.2V and 3.3V, i.e., $3.2V<U\leq3.3V$. At the second stage, the built-in lithium battery 34 is determined as low power and the indicator light is red. The third stage is the voltage $U\leq3.2V$. At the third stage, the built-in lithium battery 34 is determined as under voltage and it is determined to automatically shut down and enter into a sleep state. The high temperature upper limit value of the built-in lithium battery 34 is set to $42\pm0.5°$ C., and the low temperature control temperature upper limit value is set to $40\pm0.5°$ C. The physiotherapy device can work in a high temperature or a low temperature mode constantly through the connecting component 3.

Furthermore, the built-in lithium battery 34 provides power, and the power is stepped down and stabilized after a voltage regulator. Then, the built-in lithium battery 34 provides power to the main controller. At the same time, the lithium battery 34 also provides power for a heating main power supply circuit on the PCB 33, and the heating main power supply circuit provides the heating electrode sheet 2 with electrical energy required to generate heat. The built-in lithium battery 34 is connected to a 5V power adapter through a USB charging interface. The built-in lithium battery 34 is charged through a charging detection and management circuit. The charging detection and management circuit detects the charging input and inputs the charging signal to the main controller. The main controller then enters into a charging state when receiving the charging signal and the charging detection and management circuit determines whether the built-in lithium battery 34 is fully charged. When the voltage of the built-in lithium battery 34 reaches 4.2V, it is determined that the built-in lithium battery 34 is fully charged. During the whole charging process, the main controller will stop detecting the power button, stop the booster circuit of the voltage regulator, and turn off the main power supply circuit for heating. The main controller only performs the charging operation during the whole charging process.

In some examples, the electronic stimulator 1 may input electrical pulses into the connecting component 3 through the electric pulse transmission cable, and the connecting component 3 may transmit the electrical pulse signal to the heating electrode sheet 2, and send the electrical pulse signal to the body part of the human body through the heating electrode sheet 2.

Figure 7:
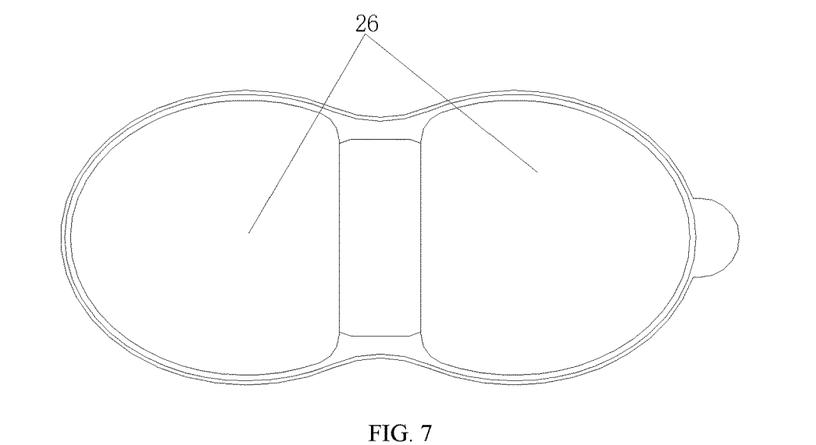
FIG. 7 is a rear view of a heating electrode sheet according to an example of the present disclosure.
Figure 8:
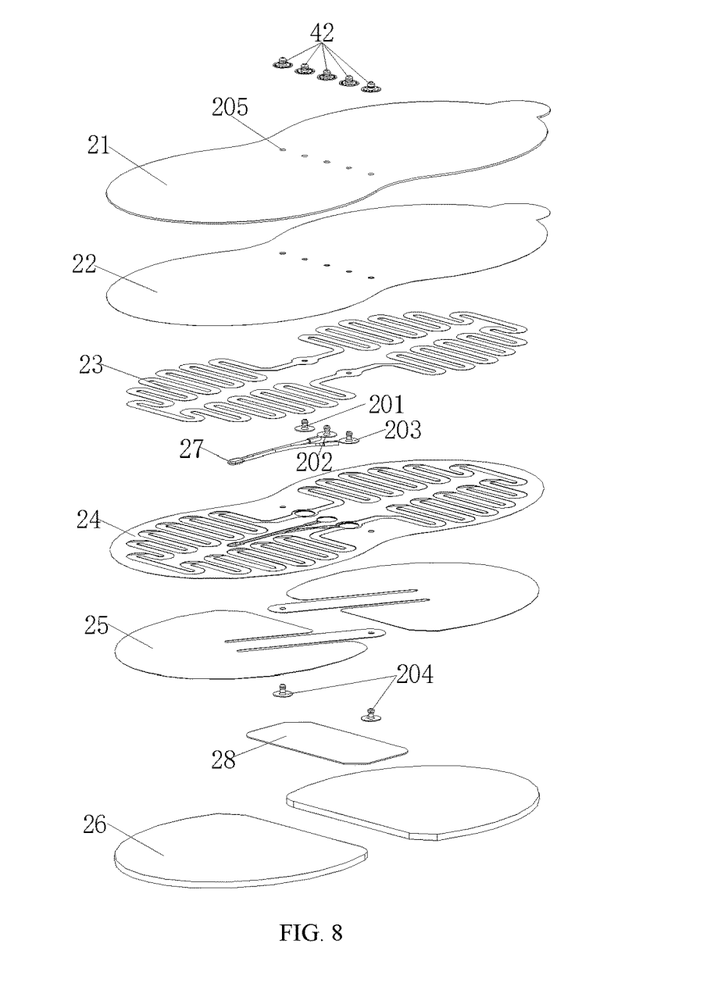
FIG. 8 is an exploded diagram of a heating electrode sheet according to an example of the present disclosure.

As shown in FIGS. 6-8, the heating electrode sheet 2 may have a symmetrical structure. The heating electrode sheet 2 may include a non-woven fabric 21, a coating bottom plate 22, a heating silver paste coating 23, a carbon layer bottom plate 24, a conductive carbon layer 25, and a conductive gel layer 26 that are arranged in sequence. The heating silver paste coating 23 is installed on the coating bottom plate 22 and the non-woven fabric 21 via a heating fastening bottom nail 201, a heat measuring fastening bottom nail 202, and a heating and heat measuring fastening bottom nail 203, as shown in FIG. 8. The carbon layer bottom plate 24 and the conductive carbon layer 25 are installed on the coating bottom plate 22 and the non-woven fabric 21 via two electric pulse fastening bottom nails 204.

In some examples, the conductive gel layer 26 are set in pairs. The conductive gel layer 26 may be respectively attached to an outer surface of the conductive carbon layer 25. Further, a plurality of second fastener holes 205 are respectively located on the middle of the non-woven fabric 21 and the coating bottom plate 22. The plurality of second fastener holes 205 are configured for installing the plurality of male fasteners 42.

Furthermore, the NTC thermistor 27 is disposed between the heating silver paste coating 23 and the carbon layer bottom plate 24. An insulating sticker 28 is placed between the conductive carbon layer 25 and the conductive gel layer 26. The insulating sticker 28 may be placed in the middle of the conductive carbon layer 25 and the conductive gel layer 26. As shown in FIG. 8, the insulating sticker 28 is place at an intermediate position of the conductive carbon layer 25 and the conductive gel layer 26.

In some examples, the heating fastening component of the heating electrode sheet 2 may transmit current through the heating silver paste coating 23 so as to heat. Further, the electric pulse fastening component may transmit the electric pulse through the conductive carbon layer 25 and the conductive gel layer 26 to act on the surface of the human skin to transmit the electric pulse. Moreover, the heat measuring fastening component connected with the NTC thermistor 27 may detect the temperature of the heating electrode sheet. Therefore, the heating electrode sheet 2 made of the non-woven fabric 21, the coating bottom plate 22, the heating silver paste coating 23, the carbon layer bottom plate 24, the conductive carbon layer 25 and the conductive gel layer 26 has a stable structure and is simple to use. The shape of the conductive carbon layer 25 is led to the center position by the fastening components and then diverges, and the conductive carbon layer 25 may be replaced by conductive silver paste.

The present disclosure connects the heating electrode sheet 2 and the connecting component 3, connects the connecting component 3 and the electric stimulator 1 via the electric pulse transmission cable, fixes the heating electrode sheet 2 on the body part that the user needs to act on, sends the electric pulse from the electric stimulator 1 and transmits the electric pulse to the connecting component 3 via the electric pulse transmission cable, transmits the electric pulse from the connecting component 3 to the heating electrode sheet 2 via the electric pulse fastening components, and transmits the electric pulse to the body part via the heating electrode sheet 2, thus implementing electric pulse treatment on the part of the skin, such as exciting neuromuscular tissue of the part of the skin, promoting local blood circulation and analgesia, and relieving anti-inflammatory, swelling, dampness and cold, pain relief, fatigue, etc.

In some examples, the physiotherapy device may include an electric stimulator capable of generating electric pulses, a heating electrode sheet capable of attaching to a user's body, and a connecting component configured to connect with the heating electrode sheet via a plurality of fastening components and configured to connect with the electric stimulator via an electric pulse transmission cable. For example, as shown in FIG. 1, the electric stimulator may be the electric stimulator 1, the heating electrode sheet may be the heating electrode sheet 2, the connecting component may be the connecting component 3.

In some examples, each fastening component may include a first fastener and a second fastener that are connected with each other, the first fastener is disposed on a midline of the connecting component and the second fastener disposed on a midline of the heating electrode sheet. For example, as shown in FIGS. 3, 6 and 8, the fastening component may be one of the fastening components 4, the first fastener may be one of the female fasteners 41, and the second fastener may be one of the male fasteners 42.

In some examples, the plurality of fastening components may include a heating fastening component, a heat measuring fastening component, and at least one electric pulse fastening component, the heating fastening component transmits current to the heating electrode sheet so as to provide heat, and the heat measuring fastening component measures a temperature of the heating electrode sheet. For examples, as shown in FIG. 8, the heating fastening component may include the heating fastening bottom nail 201, the heat measuring fastening component may include the heat measuring fastening bottom nail 202, the at least one electric pulse fastening component may include the electric pulse fastening bottom nails 204.

In some examples, the connecting component may be configured to receive the electric pulses generated by the electric stimulator via the electric pulse transmission cable, to adjust the received electric pulses, and to transmit the adjusted electric pulses via the at least one electric pulse fastening component.

In some examples, the connecting component may include a lower connecting housing and an upper connecting housing, a plurality of first fastener holes are disposed on a line in the middle of the lower connecting housing, and each first fastener hole accommodates a first fastener. For example, as shown in FIG. 5, the lower connecting housing may be the lower connecting housing 31, the upper connecting housing may be the upper connecting housing 32, the first fastener hole may be one of the first fastener holes 301.

In some examples, the connecting component may further include a PCB and a built-in lithium battery that are respectively disposed between the lower connecting housing and the upper connecting housing. As shown in FIG. 5, the PCB may be the PCB 33 and the built-in lithium battery may be the built-in lithium battery 34.

In some examples, the connecting component may further include a first side cover and a second side cover that are respectively disposed on one side of the lower connecting housing and the upper connecting housing, the first side cover may include a charging hole, a power hole that accommodates a power button, and an input hole, and the charging hole may correspond to a charging interface on the PCB, and the input hole may correspond to an electric pulse input interface on the PCB. For example, as shown in FIG. 5, the first side cover and the second side cover may be respectively the side cover 35 and the side cover 36, the charging hole may be the charging hole 303, the power hole may be the power hole 305, the input hole may be the input hole 304.

In some examples, the plurality of fastening components may include at least two fastening components, the at least two fastening components may include the heating fastening component and the at least one electric pulse fastening component, the heating fastening component transmits current to the heating electrode sheet so as to provide heat, and the at least one electric pulse fastening component transmits an electric pulse to the heating electrode sheet so as to provide the electric pulse. For examples, as shown in FIG. 8, the heating fastening component may include the heating fastening bottom nail 201, and the at least one electric pulse fastening component may include the electric pulse fastening bottom nails 204.

In some examples, the at least two fastening components may further include a heat measuring fastening component that measures temperature of the heating electrode sheet and a heating and heat measuring fastening component that transmits current to the heating electrode sheet so as to provide heat and measures temperature of the heating electrode sheet. For example, as shown in FIG. 8, the heat measuring fastening component may be the heat measuring fastening bottom nail 202, and the heating and heat measuring fastening component may be the heating and heat measuring fastening bottom nail 203.

In some examples, the heating electrode sheet may have a symmetrical structure as shown in FIGS. 6-7.

In some examples, the heating electrode sheet may include the non-woven fabric 21, the coating bottom plate 22, the heating silver paste coating 23, the carbon layer bottom plate 24, the conductive carbon layer 25, and the conductive gel layer 26 that are arranged in sequence, and the conductive gel layer 26 may include a pair of sub-layers that are respectively attached to an outer surface of the conductive carbon layer 25, as shown FIG. 8.

In some examples, the heating silver paste coating 23 may be installed on the coating bottom plate 22 and the non-woven fabric 21 via a second fastener of the heating fastening component, a second fastener of the heat measuring fastening component, and a second fastener of the heating and heat measuring fastening component. The second fastener of the heating fastening component may include the heating fastening bottom nail 201, the second fastener of the measuring fastening component may include the heat measuring fastening bottom nail 202, and the second fastener of the heating and heat measuring fastening component may include the heating and heat measuring fastening bottom nail 203, as shown in FIG. 8.

In some examples, the carbon layer bottom plate 24 and the conductive carbon layer 25 are installed on the coating bottom plate 22 and the non-woven fabric 21 via a second fastener of the electric pulse fastening component. As shown in FIG. 8, the second fastener of the electric pulse fastening component may be one of the two electric pulse fastening bottom nail 204.

In some examples, a plurality of second fastener holes are disposed in the middle of the non-woven fabric 21 and in the middle of the carbon layer bottom plate 24, and the plurality of second fastener holes respectively accommodate a second fastener. For example, as shown in FIG. 8, the plurality of second fastener holes may include the plurality of second fastener holes 205.

In some examples, an NTC thermistor may be disposed between the heating silver paste coating 23 and the carbon layer bottom plate 24, an insulating sticker 28 may be disposed between the conductive carbon layer 25 and the conductive gel layer 26, and the insulating sticker 28 may be disposed at an intermediate position between the conductive carbon layer 25 and the conductive gel layer 26, as shown in FIG. 8.

In some examples, the PCB may include a main controller, a charging management circuit, a voltage regulation circuit, a battery detection circuit and a main heating supply circuit as shown in FIG. 9.

In some examples, a method for controlling a physiotherapy device may include: providing an electric stimulator capable of generating electric pulses; providing a heating electrode sheet capable of attaching to a user's body; providing a connecting component configured to connect with the heating electrode sheet via a plurality of fastening components and configured to connect with the electric stimulator via an electric pulse transmission cable; providing each fastening component including a first fastener and a second fastener that are connected with each other, disposing the first fastener on a midline of the connecting component and disposing the second fastener on a midline of the heating electrode sheet; providing the plurality of fastening components including a heating fastening component, a heat measuring fastening component, and at least one electric pulse fastening component, where the heating fastening component transmits current to the heating electrode sheet so as to provide heat, and the heat measuring fastening component measures a temperature of the heating electrode sheet; and configuring the connecting component to receive the electric pulses generated by the electric stimulator via the electric pulse transmission cable, to adjust the received electric pulses, and to transmit the adjusted electric pulses via the at least one electric pulse fastening component.

For example, as shown in FIG. 1, the electric stimulator may be the electric stimulator 1, the heating electrode sheet may be the heating electrode sheet 2, the connecting component may be the connecting component 3. As shown in FIGS. 3, 6 and 8, the fastening component may be one of the fastening components 4, the first fastener may be one of the female fasteners 41, and the second fastener may be one of the male fasteners 42. As shown in FIG. 8, the heating fastening component may include the heating fastening bottom nail 201, the heat measuring fastening component may include the heat measuring fastening bottom nail 202, the at least one electric pulse fastening component may include the electric pulse fastening bottom nails 204.

In some examples, the method may further include: providing the connecting component including a lower connecting housing and an upper connecting housing; disposing a plurality of first fastener holes on a line in the middle of the lower connecting housing; and accommodating each first fastener hole with a first fastener. For example, as shown in FIG. 5, the lower connecting housing may be the lower connecting housing 31, the upper connecting housing may be the upper connecting housing 32, the first fastener hole may be one of the first fastener holes 301.

In some examples, the method may further include providing the connecting component including a PCB and a built-in lithium battery that are respectively disposed between the lower connecting housing and the upper connecting housing. As shown in FIG. 5, the PCB may be the PCB 33 and the built-in lithium battery may be the built-in lithium battery 34.

In some examples, the method may further include: providing the connecting component further including a first side cover and a second side cover that are respectively disposed on one side of the lower connecting housing and the upper connecting housing; and providing the first side cover including a charging hole, a power hole that accommodates a power button, and an input hole, where the charging hole corresponds to a charging interface on the PCB, and the input hole corresponds to an electric pulse input interface on the PCB. For example, as shown in FIG. 5, the first side cover and the second side cover may be respectively the side cover 35 and the side cover 36, the charging hole may be the charging hole 303, the power hole may be the power hole 305, the input hole may be the input hole 304.

In some examples, the method may further include: providing the plurality of fastening components including at least two fastening components; and providing the at least two fastening components including a heating fastening component and an electric pulse fastening component, where the heating fastening component transmits current to the heating electrode sheet so as to provide heat, and the electric pulse fastening component transmits an electric pulse to the heating electrode sheet so as to provide the electric pulse. For examples, as shown in FIG. 8, the heating fastening component may include the heating fastening bottom nail 201, and the at least one electric pulse fastening component may include the electric pulse fastening bottom nails 204.

In some examples, the method may further include: providing the at least two fastening components further including a heat measuring fastening component that measures temperature of the heating electrode sheet and a heating and heat measuring fastening component that transmits current to the heating electrode sheet so as to provide heat and measures temperature of the heating electrode sheet. For example, as shown in FIG. 8, the heat measuring fastening component may be the heat measuring fastening bottom nail 202, and the heating and heat measuring fastening component may be the heating and heat measuring fastening bottom nail 203.

In some examples, the method may further include: providing the heating electrode sheet with a symmetrical structure as shown in FIGS. 6-7; providing the heating electrode sheet including the non-woven fabric 21, the coating bottom plate 22, the heating silver paste coating 23, the carbon layer bottom plate 24, the conductive carbon layer 25, and the conductive gel layer 26 that are arranged in sequence; and providing the conductive gel layer 26 including a pair of sub-layers that are respectively attached to an outer surface of the conductive carbon layer 25, as shown in FIG. 8.

In some examples, the method may further include: providing the heating silver paste coating 23 installed on the coating bottom plate 22 and the non-woven fabric 21 via a second fastener of the heating fastening component, a second fastener of the heat measuring fastening component, and a second fastener of the heating and heat measuring fastening component; and providing the carbon layer bottom plate 24 and the conductive carbon layer installed on the coating bottom plate and the non-woven fabric via a second fastener of the electric pulse fastening component. The second fastener of the heating fastening component may include the heating fastening bottom nail 201, the second fastener of the measuring fastening component may include the heat measuring fastening bottom nail 202, the second fastener of the heating and heat measuring fastening component may include the heating and heat measuring fastening bottom nail 203, and the second fastener of the electric pulse fastening component may be one of the two electric pulse fastening bottom nail 204, as shown in FIG. 8.

In some examples, the method may further include: providing a plurality of second fastener holes disposed in the middle of the non-woven fabric 21 and in the middle of the carbon layer bottom plate 24; and respectively accommodating the plurality of second fastener holes with a second fastener. For example, as shown in FIG. 8, the plurality of second fastener holes may include the plurality of second fastener holes 205.

The description of the present disclosure has been presented for purposes of illustration and is not intended to be exhaustive or limited to the present disclosure. Many modifications, variations, and alternative implementations will be apparent to those of ordinary skill in the art having the benefit of the teachings presented in the foregoing descriptions and the associated drawings.

The examples were chosen and described in order to explain the principles of the disclosure and to enable others skilled in the art to understand the disclosure for various implementations and to best utilize the underlying principles and various implementations with various modifications as are suited to the particular use contemplated. Therefore, it is to be understood that the scope of the disclosure is not to be limited to the specific examples of the implementations disclosed and that modifications and other implementations are intended to be included within the scope of the present disclosure.

What is claimed is:

1. A physiotherapy device, comprising:
   an electric stimulator capable of generating electric pulses;
   a heating electrode sheet capable of attaching to a user's body, wherein the heating electrode sheet comprises a plurality of layers that are arranged in a sequence of a non-woven fabric, a coating bottom plate, a heating silver paste coating, a carbon layer bottom plate, a conductive carbon layer, and a conductive gel layer; and
   a connecting component configured to connect with the heating electrode sheet via a plurality of fastening components and configured to connect with the electric stimulator via an electric pulse transmission cable,
   wherein each fastening component comprises a first fastener and a second fastener that are connected with each other, the first fastener is disposed on a midline of the connecting component and the second fastener disposed on a midline of the heating electrode sheet,
   wherein the plurality of fastening components comprise a heating fastening component, a heat measuring fastening component, and at least one electric pulse fastening component, the heating fastening component transmits current to the heating electrode sheet so as to provide heat, and the heat measuring fastening component measures a temperature of the heating electrode sheet, and
   wherein the connecting component is configured to receive the electric pulses generated by the electric stimulator via the electric pulse transmission cable, to adjust the received electric pulses, and to transmit the adjusted electric pulses via the at least one electric pulse fastening component.

2. The physiotherapy device of claim 1, wherein the connecting component comprises a lower connecting housing and an upper connecting housing, a plurality of first fastener holes are disposed on a line in the middle of the lower connecting housing, and each first fastener hole accommodates a first fastener.

3. The physiotherapy device of claim 2, wherein the connecting component further comprises a printed circuit board (PCB) and a built-in lithium battery that are respectively disposed between the lower connecting housing and the upper connecting housing.

4. The physiotherapy device of claim 3, wherein the connecting component further comprises a first side cover and a second side cover that are respectively disposed on one side of the lower connecting housing and the upper connecting housing,
   wherein the first side cover comprises a charging hole, a power hole that accommodates a power button, and an input hole, and
   wherein the charging hole corresponds to a charging interface on the PCB, and the input hole corresponds to an electric pulse input interface on the PCB.

5. The physiotherapy device of claim 1, wherein the plurality of fastening components comprises at least two fastening components, the at least two fastening components comprise the heating fastening component and the at least one electric pulse fastening component, the heating fastening component transmits current to the heating electrode sheet so as to provide heat, and the at least one electric pulse fastening component transmits an electric pulse to the heating electrode sheet so as to provide the electric pulse.

6. The physiotherapy device of claim 5, wherein the at least two fastening components further comprise a heat measuring fastening component that measures temperature of the heating electrode sheet, and a heating and heat measuring fastening component that transmits current to the heating electrode sheet so as to both provide heat and measure temperature of the heating electrode sheet.

7. The physiotherapy device of claim 6, wherein the heating electrode sheet has a symmetrical structure, and
   wherein the conductive gel layer comprises a pair of sub-layers that are respectively attached to an outer surface of the conductive carbon layer.

8. The physiotherapy device of claim 7, wherein the heating silver paste coating is installed on the coating bottom plate and the non-woven fabric via a second fastener of the heating fastening component, a second fastener of the heat measuring fastening component, and a second fastener of the heating and heat measuring fastening component, and wherein the carbon layer bottom plate and the conductive carbon layer are installed on the coating bottom plate and the non-woven fabric via a second fastener of the electric pulse fastening component.

9. The physiotherapy device of claim 8, wherein a plurality of second fastener holes are disposed in the middle of the non-woven fabric and in the middle of the carbon layer bottom plate, and the plurality of second fastener holes respectively accommodate a second fastener.

10. The physiotherapy device of claim 8, wherein a negative temperature coefficient (NTC) thermistor is disposed between the heating silver paste coating and the carbon layer bottom plate, and an insulating sticker is disposed between the conductive carbon layer and the conductive gel layer, and wherein the insulating sticker is disposed at an intermediate position between the conductive carbon layer and the conductive gel layer.

11. The physiotherapy device of claim 3, wherein the PCB comprises a main controller, a charging management circuit, a voltage regulation circuit, a battery detection circuit and a main heating supply circuit.

12. A method for controlling a physiotherapy device, comprising:
providing an electric stimulator capable of generating electric pulses;
providing a heating electrode sheet capable of attaching to a user's body, wherein the heating electrode sheet comprises a plurality of layers that are arranged in a sequence of a non-woven fabric, a coating bottom plate, a heating silver paste coating, a carbon layer bottom plate, a conductive carbon layer, and a conductive gel layer;
plurality of fastening components and configured to connect with the electric stimulator via an electric pulse transmission cable;
providing each fastening component comprising a first fastener and a second fastener that are connected with each other, disposing the first fastener on a midline of the connecting component and disposing the second fastener on a midline of the heating electrode sheet;
providing the plurality of fastening components comprising a heating fastening component, a heat measuring fastening component, and at least one electric pulse fastening component, wherein the heating fastening component transmits current to the heating electrode sheet so as to provide heat, and the heat measuring fastening component measures a temperature of the heating electrode sheet; and
configuring the connecting component to receive the electric pulses generated by the electric stimulator via the electric pulse transmission cable, to adjust the received electric pulses, and to transmit the adjusted electric pulses via the at least one electric pulse fastening component.

13. The method of claim 12, further comprising:
providing the connecting component comprising a lower connecting housing and an upper connecting housing;
disposing a plurality of first fastener holes on a line in the middle of the lower connecting housing; and
accommodating each first fastener hole with a first fastener.

14. The method of claim 13, further comprising:
providing the connecting component comprising a printed circuit board (PCB) and a built-in lithium battery that are respectively disposed between the lower connecting housing and the upper connecting housing.

15. The method of claim 14, further comprising:
providing the connecting component further comprising a first side cover and a second side cover that are respectively disposed on one side of the lower connecting housing and the upper connecting housing; and
providing the first side cover comprising a charging hole, a power hole that accommodates a power button, and an input hole, wherein the charging hole corresponds to a charging interface on the PCB, and the input hole corresponds to an electric pulse input interface on the PCB.

16. The method of claim 12, further comprising:
providing the plurality of fastening components comprising at least two fastening components; and
providing the at least two fastening components comprising a heating fastening component and an electric pulse fastening component, wherein the heating fastening component transmits current to the heating electrode sheet so as to provide heat, and the electric pulse fastening component transmits an electric pulse to the heating electrode sheet so as to provide the electric pulse.

17. The method of claim 16, further comprising:
providing the at least two fastening components further comprising a heat measuring fastening component that measures temperature of the heating electrode sheet, and a heating and heat measuring fastening component that transmits current to the heating electrode sheet so as to both provide heat and measure temperature of the heating electrode sheet.

18. The method of claim 17, further comprising:
providing the heating electrode sheet with a symmetrical structure;
and
providing the conductive gel layer comprising a pair of sub-layers that are respectively attached to an outer surface of the conductive carbon layer.

19. The method of claim 18, further comprising:
providing the heating silver paste coating installed on the coating bottom plate and the non-woven fabric via a second fastener of the heating fastening component, a second fastener of the heat measuring fastening component, and a second fastener of the heating and heat measuring fastening component; and
providing the carbon layer bottom plate and the conductive carbon layer installed on the coating bottom plate and the non-woven fabric via a second fastener of the electric pulse fastening component.

20. The method of claim 19, further comprising:
providing a plurality of second fastener holes disposed in the middle of the non-woven fabric and in the middle of the carbon layer bottom plate; and
respectively accommodating the plurality of second fastener holes with a second fastener.

* * * * *